(12) United States Patent
Yachia et al.

(10) Patent No.: US 11,083,868 B2
(45) Date of Patent: Aug. 10, 2021

(54) SYSTEM FOR INHIBITING BIOFILM FORMATION ON CATHETERS, OTHER INDWELLING OR IMPLANTABLE DEVICES AND OTHER DEVICES

(71) Applicant: Innoventions LTD., Or Akiva (IL)

(72) Inventors: Daniel Yachia, Herzlia (IL); Valentin Ponomarenko, Haifa (IL); Yaara Arbel, Bet Rimon (IL); Ortal Natanel Shtiglitz, Tel Aviv (IL); Yehonatan Mathis, Or-Akiva (IL)

(73) Assignee: Innoventions Ltd., Or Akiva (IL)

( * ) Notice: Subject to any disclaimer, the term of this patent is extended or adjusted under 35 U.S.C. 154(b) by 548 days.

(21) Appl. No.: 15/573,245

(22) PCT Filed: May 11, 2016

(86) PCT No.: PCT/IL2016/050502
§ 371 (c)(1),
(2) Date: Nov. 10, 2017

(87) PCT Pub. No.: WO2016/181397
PCT Pub. Date: Nov. 17, 2016

(65) Prior Publication Data
US 2018/0117279 A1 May 3, 2018

Related U.S. Application Data

(60) Provisional application No. 62/160,651, filed on May 13, 2015.

(51) Int. Cl.
*A61M 25/00* (2006.01)
*A61L 29/02* (2006.01)
(Continued)

(52) U.S. Cl.
CPC ......... *A61M 25/0026* (2013.01); *A61L 29/02* (2013.01); *A61L 29/16* (2013.01);
(Continued)

(58) Field of Classification Search
CPC .. A61M 2025/0036; A61M 2025/0037; A61M 2025/004; A61M 2025/0048;
(Continued)

(56) References Cited

U.S. PATENT DOCUMENTS 5,458,575 A * 10/1995 Wang ................. A61M 25/1011
604/101.02
5,820,607 A * 10/1998 Tcholakian ............. A61L 29/06
604/265

(Continued)

FOREIGN PATENT DOCUMENTS

CA          2073509        7/1991
WO    WO 2012/096787      7/2012

OTHER PUBLICATIONS

S. Saint, B. Lipsky, S. Goold., "Indwelling Urinary Catheters: A One-Point Restraint?", Annals Internal Medicine, Jul. 2002, vol. 137(2), pp. 125-127.

(Continued)

Primary Examiner — Jason E Flick
(74) Attorney, Agent, or Firm — Robert G. Lev (57) ABSTRACT

Devices for preventing and/or otherwise inhibiting biofilm formation include a lumen and/or a cavity coupled with a wall configured for holding oils, which leach through the wall of the devices to a surface, the oils at the surface creating a smooth surface coating.

32 Claims, 10 Drawing Sheets

(51) Int. Cl.
*A61L 29/16* (2006.01)
*A61M 25/10* (2013.01)

(52) U.S. Cl.
CPC ...... *A61M 25/007* (2013.01); *A61M 25/0017* (2013.01); *A61M 25/0043* (2013.01); *A61M 25/0045* (2013.01); *A61M 25/1025* (2013.01); *A61L 2300/22* (2013.01); *A61L 2300/452* (2013.01); *A61M 25/0023* (2013.01); *A61M 25/0074* (2013.01); *A61M 2025/004* (2013.01); *A61M 2025/0036* (2013.01); *A61M 2025/0037* (2013.01); *A61M 2025/0048* (2013.01); *A61M 2025/0056* (2013.01)

(58) Field of Classification Search
CPC .. A61M 2025/0056; A61M 2025/0057; A61M 25/0026; A61M 25/0045; A61M 2205/0205; A61M 2205/0238; A61M 25/0017; A61M 25/0023; A61M 25/0043; A61M 25/007; A61M 25/0074; A61M 25/1025; A61L 2300/22; A61L 2300/452; A61L 29/02; A61L 29/16
See application file for complete search history.

(56) References Cited

U.S. PATENT DOCUMENTS

| | | | |
|---|---|---|---|
| 6,413,203 B1* | 7/2002 | Sahatjian | A61M 25/104 600/3 |
| 7,635,358 B2 | 12/2009 | Tan | |
| 7,691,082 B2* | 4/2010 | Shippy, III | A61M 25/1002 604/103.08 |
| 8,668,667 B2* | 3/2014 | Chappa | A61L 29/16 604/101.02 |
| 2011/0146680 A1* | 6/2011 | Conway | A61L 29/16 128/204.18 |

OTHER PUBLICATIONS

Johnson et al. "Activities of a Nitrofurazone-containing Urinary Catheter and a Silver Hydrogel Catheter Against Multidrug-resistant Bacteria Characteristic of Catheter-associated Urinary Tract Infection",Antimicrob. Agents Chemother. Dec. 1999 43(12), pp. 2990-2995.

* cited by examiner

SYSTEM FOR INHIBITING BIOFILM FORMATION ON CATHETERS, OTHER INDWELLING OR IMPLANTABLE DEVICES AND OTHER DEVICES

CROSS-REFERENCES TO RELATED APPLICATIONS

This application is related to and claims priority from commonly owner U.S. Provisional Patent Application Ser. No. 62/160,651, entitled: SYSTEM FOR INHIBITING BIOFILM FORMATION ON CATHETERS AND OTHER INDWELLING OR IMPLANTABLE DEVICES, filed on May 13, 2015, the disclosure of which is incorporated by reference herein, in its entirety. This application is a National Phase Application of International Application PCT/IL2016/050502 filed on May 11, 2016.

TECHNICAL FIELD

The present invention, in some embodiments thereof, relates to inhibiting biofilm formation on catheters and other implants or indwelling devices.

BACKGROUND

Biofilms are complex aggregations of microorganisms which grow on a solid surface or matrix which appeared on the Earth 4.5 billion years ago. For example, biofilms typically form on the surfaces of indwelling catheters and other indwelling devices or implants. It is estimated that 65% of the bacterial infections treated in hospitals are caused by bacterial biofilms.

These biofilms are typically resistant to antibiotics. Currently, there are not any proven effective strategies, which prevent/inhibit biofilm formation.

Biofilm formation causes chronic infection for people who require regular catheterizations or have implanted devices. This is especially prevalent with urinary catheters. In patients with an indwelling urethral catheter, the daily rate of acquisition of bacteriuria is 3% to 10%, as reported in Saint S, Lipsky B. Goold S., in *"Indwelling urinary catheters: a one-point restraint?"*, Ann. Intern. Med., July 2002, 137(2), pages 125-127. For example, in the United States alone there are over 200 Million urinary catheterizations in a year, with more than one million reported cases of catheter-associated urinary tract infection (CAUTI). Many of these CAUTI cases involve biofilms forming on the indwelling urinary catheter, the biofilms consisting of adherent microorganisms, their extracellular products, and host components, all of which are deposited on the catheter. These biofilms cause persistent infections that are resistant to antimicrobial therapy, for which proven effective strategies for prevention CAUTI or other biofilm caused infections from catheterization are presently lacking.

Attempts have been made to inhibit bacterial growth from catheters by impregnating urinary catheters with antimicrobial agents, such as nitrofurazone. However, these treated catheters merely delayed the onset of bacteriuria in chronically catheterized patients, as reported in Johnson J, et al., in *"Activities of a nitrofurazone-containing urinary catheter and a silver hydrogel catheter against multidrug-resistant bacteria characteristic of catheter-associated urinary tract infection"*, Antimicrob. Agents Chemother. 1999 December, 43(12), pages 2990-2995, Accordingly, this was a potentially effective solution in preventing bacteriuria for patients undergoing short-term catheterization, but failed to be effective over the long term, with chronically catheterized patients.

Additionally, attempts were made to coat catheters with impregnated agents. However, these coatings tend to wear off, become covered with dirt, ultimately becoming ineffective. Other attempts at treating catheters to make them bactericidal, have included, modifying the polymeric surface of polymeric catheters through glow discharge techniques, as well as making the catheters of various combinations of polymeric materials. However, the problems associated is with biofilm bacteria remain.

Figure 16:
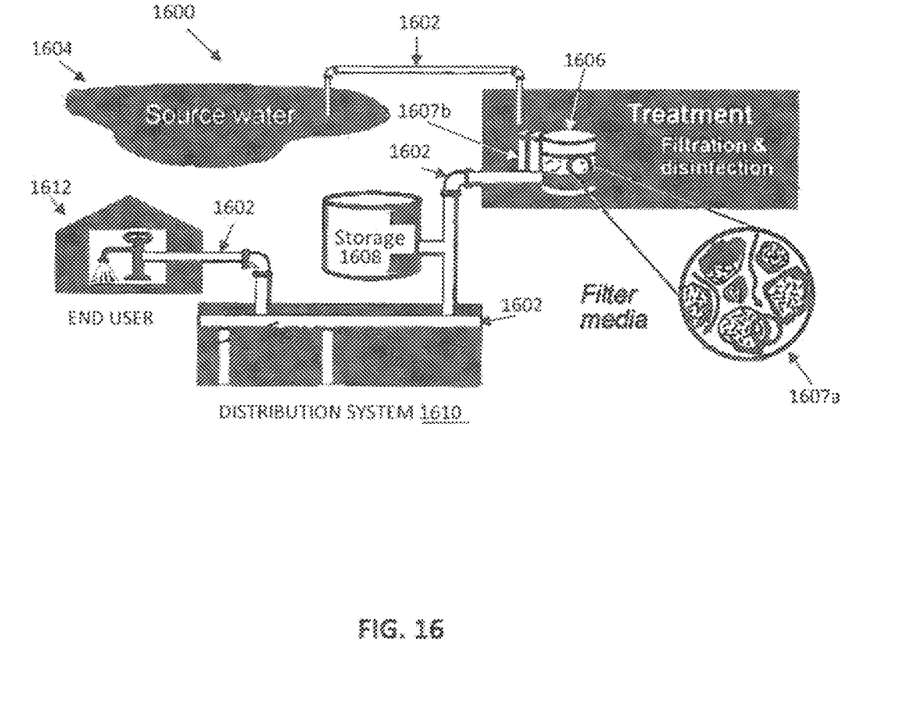

Biofilm formation is also a problem in water distribution systems, such as that shown in FIG. 16. These treatment systems 1600 are formed of pipes 1602 that extend from a water source 1604, to a treatment system 1606 (which includes multiple filter 1607*a* and disinfectant units 1607*b*) to a storage tank 1608, to a distribution system 1610, before entering the plumbing system and outlet of 1612 of the end user, such as a domestic consumer. Biofilms can also form in industrial water and sewer transport pipes, as well as in brine and, waste-water transport tankers and pipes, In addition, biofilm formation in water reservoirs, water based liquid food transporting tankers, trucks and ship hulls may create a serious health problem.

Biofilms are an ideal media for harboring legionella microbes that contaminate water supplies, as they protect bacteria against disinfectants, other anti microbial agents. When biofilms are in municipal water systems, they include for example, aggregates of microorganisms, such as bacteria, fungi, diatoms, protozoa, algae, and any exogenous materials, which are embedded in a hydrated extracellular matrix and attached to a solid surface, such as that of the pipes 1602 and filters of the Treatment System 1606. These biofilms also include live and dead bacteria, as well as organic and inorganic matter.

These biofilms cause conditions such as pipe fouling, as seen in the food industry, paper mills, water distribution systems, cooling towers. Moreover, Biofilms negatively affect industrial settings, causing corrosion and lime scale buildup. When in pipes, the corrosion and lime scale reduces liquid flow through the pipe, as well as reduces thermal conduction from the liquid to the outer pipe shell. This reduces the pipes' overall thermal efficiency when used as a heat exchanger.

SUMMARY OF THE INVENTION

According to some embodiments of the present invention, catheters and other indwelling devices include a lumen and/or cavity coupled with a wall configured for holding oils, such as mineral oil and other oil-based substances (collectively "oil" or "oils" as used throughout this document) while allowing the oil to leach through the wall of the catheter or device to the surface, the oil at the surface creating a smooth surface (e.g., coating on the surface) with zero stress inhibiting and/or presenting biofilm formation, hence, significantly toweling the possibility for biofilm and bacterial adhesions on the catheter or device and causing infections. The walls are such that they are of materials at various thicknesses and porosities to allow for oil leaching therethrough. Additionally, the catheters and devices of the present invention typically include a method to create smooth exterior surfaces, as biofilm growth tends to be inhibited by such smooth surfaces, due to their being zero stress on these surfaces.

The present invention creates articles, such as tubes, conduits, pipes and other devices, of silicone walls/channels/cells, that based on the natural and/or modified porosity of the silicone, allows oil to leach from within the tubes/channels/cells to the article surface, to prevent, inhibit or otherwise delay biofilm formation. As used herein, the term "leach" refers to the movement of oil through a material in a process involving an interaction between the oil and the material.

The present invention is also usable in municipal water systems, along with other systems which transport water and other materials. For example, the present invention provides a clean, safe and sanitized water supply, which is important in ensuring public health. The present invention serves to effectively reduce biofilm as-well-as scale build-up which serve as sites for hosting harmful pathogens such as E. coli, Pseudomonas or Salmonella. This is especially true in water carrying pipes and water reservoirs, for assuring public health.

The present invention provides oily surfaces, for example, in pipes and other conduits, which carry liquids and the like, which increase flow velocity and shear force to biofilms and decrease sedimentation. As a result, water based liquids move efficiently through the aforementioned pipes and conduits, treated, or constructed in accordance with the invention, than with conventional pipes. Accordingly, the invention reduces deposits which gives rise to biofilm formation and buildup.

Embodiments of the invention are directed to tubes, such as a tube comprising a body, e.g., in a tubular or cylindrical shape. The tube is usable, for example, in surgical and medical applications, but is also usable non-medical applications. A lumen extends through the inside of the body. The lumen is bounded at least in part by an outer wall of the body, and, the outer wall of the body is configured for accommodating oil leaching through the outer wall of the body and onto the outer surface of the outer wall of the body.

Optionally, the lumen extends along the outer wall of the body.

Optionally, the lumen extends along the outer wall of the body in at least one of a longitudinal orientation, a spiral orientation, and a zig-zag orientation.

Optionally, the tube is such that lumen is filled with oil.

Optionally, the lumen includes: a central lumen extending through the body, and at least one internal lumen intermediate the central lumen and the outer wall of the body, the portion of the central lumen bordering the at least one inner lumen defining an inner wall configured for accommodating oil leaching through the inner wall and onto the inner surface of the central lumen.

Optionally, the at least one internal lumen is filled with oil.

Optionally, the oil includes oil-based substances.

Optionally, the inner wall, and the outer wall are of a material of a porosity to accommodate oil leaching from the inner lumen through the inner wall to the surface of the inner wall and through the outer wall to the surface of the outer wall.

Embodiments of the invention are directed to a device, for example, for preventing biofilm formation. The device comprises; an external surface covered with a silicone membrane under which oil is filled, the silicone membrane configured to accommodate the oil leaching therethrough to the surface of the silicon membrane.

Optionally, the device is at least one of an implantable device or an indwelling device.

Optionally, the oil includes oil-based substances.

Optionally, the silicone membrane is of a porosity to accommodate oil leaching therethrough to the surface of the silicone membrane.

Embodiments of the present invention are directed to a device, for example, for preventing biofilm formation. The device comprises: a double layer membrane configured for leaching oil therethrough, in which oil is filled between the layers.

Optionally, the membrane includes silicone.

Optionally, the silicone membrane device is at least one of an implantable device or an indwelling device.

Optionally, the oil includes oil-based substances.

Optionally, the double layer membrane is of a porosity to accommodate oil leaching therethrough to the surface of the device.

Embodiments of the invention are directed to a conduit. The conduit comprises: an outer tubular member; and, an inner surface including a plurality of channels extending along the tubular member, the inner surface of a material configured for leaching oil therethrough, when the channels are filled with oil.

Optionally, the channels are oriented substantially parallel to each other and extend along the length of the outer tubular member.

Optionally, the channels are oriented in a spiraling manner along the length of the outer tubular member.

Optionally, the channels oriented in a spiraling manner include a single channel oriented in a spiraling manner.

Optionally, the channels oriented, in a spiraling manner include multiple channels oriented in a spiraling manner.

Optionally, the outer tubular member includes an outer layer in communication with an inner layer defining the inner surface.

Optionally, the outer tubular member and the inner surface are coextruded.

Optionally, the channels are filled with oil.

Optionally, the conduit includes at least one of tubes and pipes.

Optionally the material of the conduit is of a porosity for accommodating oil to leach therethrough and coat the inner surface.

Embodiments of the invention are also directed to a method for inhibiting biofilm formation in a structure. The method comprises: providing a structure, including at least one lumen for holding oil, the structure including at least one member defining a side of the at least one lumen, the at least one member of a material configured for leaching the oil through the at least one member to the outer surface of the at least one member, when the at least one lumen is filled with the oil; and, filling the at least one lumen with oil.

Optionally, the structure includes at least one of: implantable medical devices, indwelling catheters, medical tubes, medical conduits, non-medical tubes, non-medical conduits and pipes.

Optionally, the method additionally comprises: deploying the structure to a designated site.

Optionally, the oil includes oil-based substances.

Optionally, the oil-based substances include at least one of: medical grade mineral oils, mineral oils, and vegetable oils.

Optionally, the material is of a porosity for accommodating oil to leach therethrough to the outer surface of the material.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described, below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings, where like reference numerals or characters represent corresponding or like elements. With specific reference now to the drawings in detail, it is in stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 12A is a cross-sectional longitudinal view of the catheter of FIG. 1 with an alternative embodiment connector of FIG. 4A;

FIG. 12B is a cross sectional view detailing the vent at the connector of the catheter of FIG. 12A;

FIG. 12C is across-sectional view showing the manifold at the tip of the catheter of FIG. 12A;

DETAILED DESCRIPTION

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1:
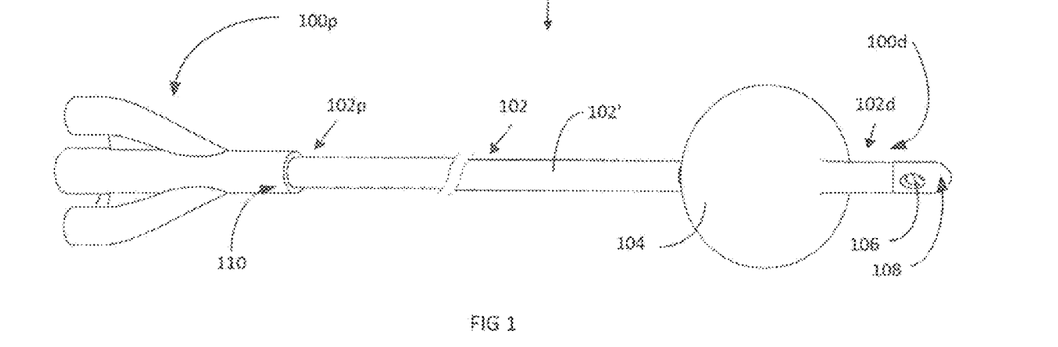
FIG. 1 shows an isometric view of a self-retaining catheter in accordance with embodiments of the present invention.

FIG. 1 shows an apparatus, in the exemplary form of a catheter 100, in accordance with embodiments of the present invention. This catheter 100 is exemplary of the present invention, as the present invention is also embodied in other devices, including indwelling or implanted devices for the human and/or animal body.

The catheter 100 is, for example, a self-retaining urinary catheter, such as "Foley" catheter. The catheter 100 includes a proximal end 100p, and distal end 100d, The distal end 100d of the catheter 100, which also defines the distal end 102d of the body 102, is, for example, for positioning inside the requisite body opening, tube, orifice, or the like, while the proximal end 100p, which includes a connector 110, that attaches to the body 102 (at the proximal end 102p of the body 102), remains outside of the human or animal body. The catheter 100 includes a body 102, which supports a balloon 104 (shown in an inflated state) and includes an opening 106 to the ambient environment (through which urine and other bodily fluids enter the catheter 100 for drainage) at a tip 108, formed at the distal end 100d. The body 102, at its distal end 102d, terminates at the tip 108, with the tip 108 defining the distal end 100d of the catheter 100.

Figure 2A:
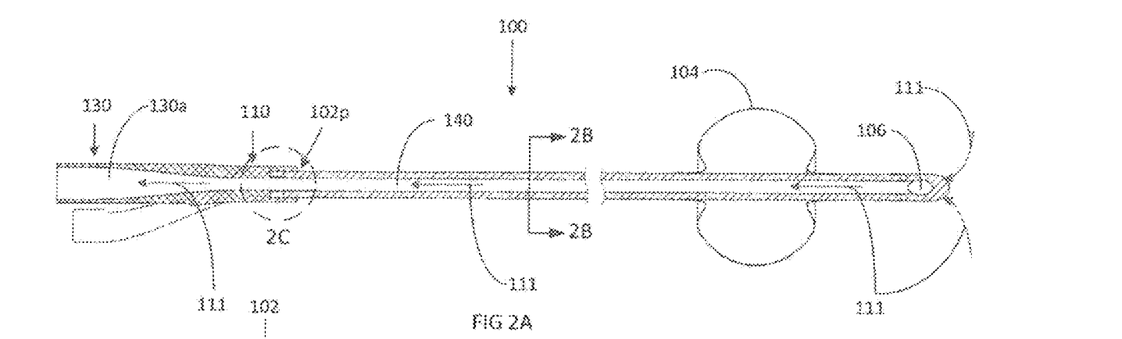
FIG. 2A shows a longitudinal cross-section of a self-retaining catheter in accordance with embodiments of the present invention.

As shown in FIG. 2A, urine and other bodily fluids flow through the catheter 100 in accordance with the arrows 111. The fluids enter the catheter 100 through the opening 106 in the tip 108, flow through the central lumen 140 of the body 102 of the catheter 100 (shown in FIG. 2B), and then flow through the lumen 130a of the connector 110, and leave the catheter 100 via the port 130.

The tip 108 typically may be made of a polymeric material, which, may be harder than the material for the body 102, as detailed below. The proximal end of the body 102p terminates at the connector 110.

Figure 3A:
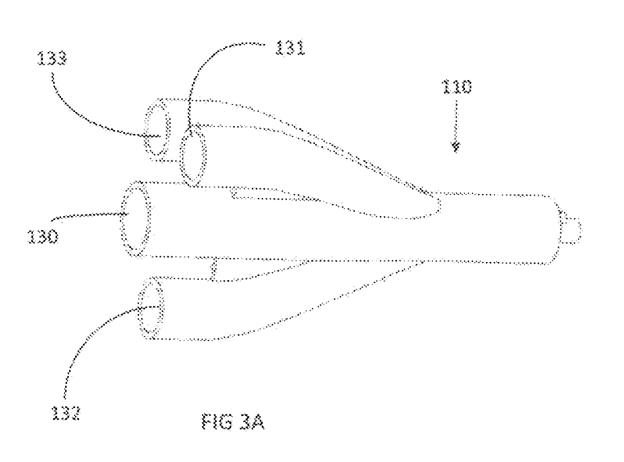
FIG. 3A shows an isometric view of the connector of the catheter of FIG. 1.
Figure 3B:
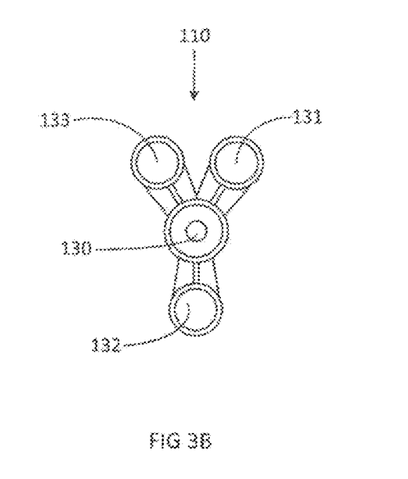
FIG. 3B shows a front view of the connector of the catheter of FIG. 3A.

The connector 110 includes ports 130-133, as shown in FIGS. 3A and 3B, to which attention is also directed. The connector 110 is typically made of a polymeric material compatible with the material of the body 102, and is joined to the body 102 by conventional materials joining techniques.

The ports 130-133 include a central port 130 and central lumen 130a, through which the central lumen 140 of the body 102 is accessed. Outer ports 131-133 include an oil filling port 131 and lumen 131a, through which oil for the oil filling lumen 141 enters the catheter 100, an air vent 132 including a lumen 132a joining to lumens 142 by the upper manifold 150b for air outflow through the vent (as shown in FIG. 2C), a balloon, port 133 and lumen 133a, through which the balloon lumen 143 is accessed (for example, by instrumentation) for inflating and deflating the balloon 104.

Figures 4A, 4B:
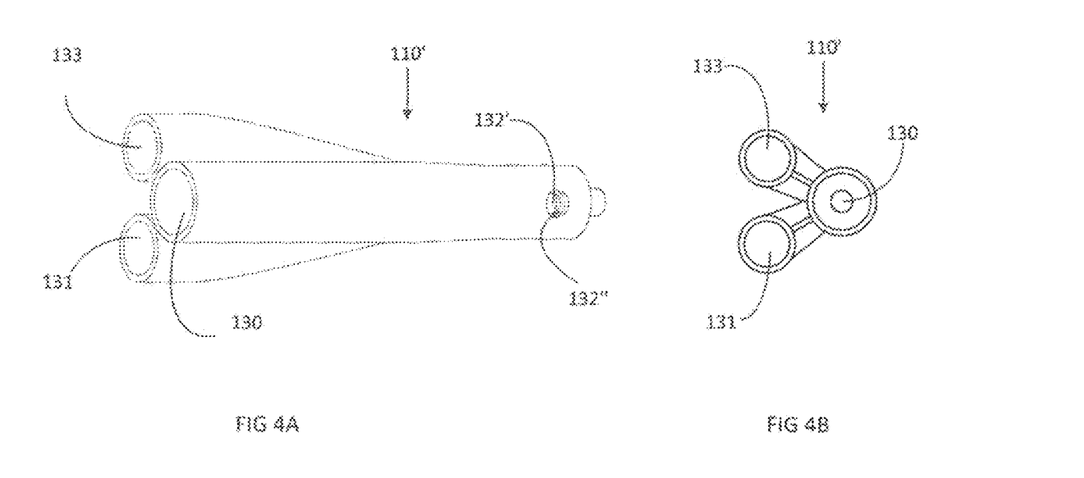
FIG. 4A shows an isometric view of an alternative embodiment of the connector of the catheter of FIG. 1.
FIG. 4B shows a front view of the connector of the catheter of FIG. 4A.
Figures 12A, 12B, 12C:
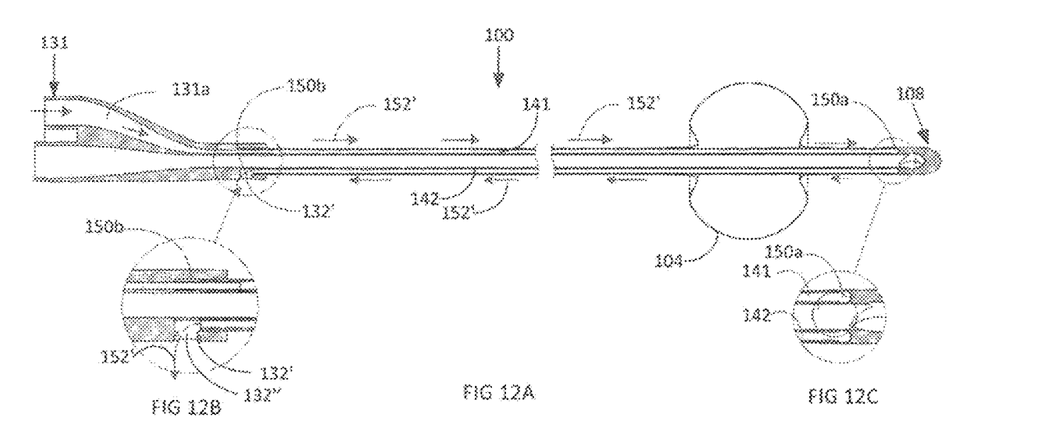

FIGS. 4A and 4B show an alternative embodiment of the connector 110'. Here, the vent 132', which connects to the upper manifold 150b, extends to the ambient environment (through the vent port 132") from the oil lumens 142 of the body 102 (FIG. 12B). Similar to that for the connector 110, the port 130 includes a central port 130 and central lumen 130a, through which the central lumen 140 of the body 102 is accessed. Outer ports 131, 133 include an oil filling port 131 and lumen 131a, through which oil for the oil filling lumen 141 enters the catheter 100, and, a balloon port 133 and lumen 133a, through which the balloon lumen 143 is accessed (for example, by instrumentation) for inflating and deflating the balloon 104.

Figure 2B:
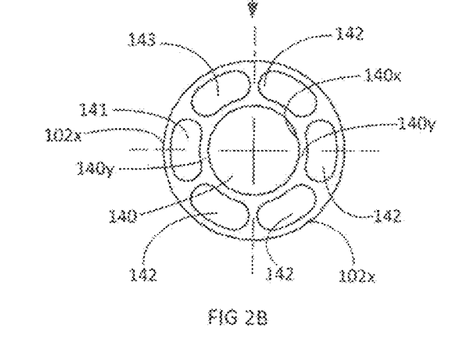
FIG. 2B is a cross-sectional view of the catheter of FIGS. 1 and 2A, taken along line 2B-2B of FIG. 2A.
Figure 2C:
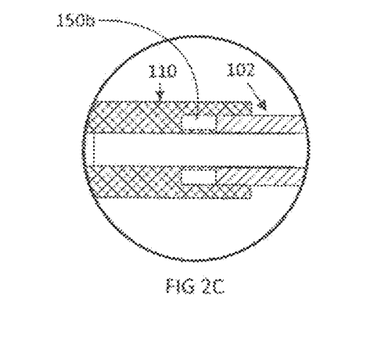
FIG. 2C is a detail view of the vent manifold of the catheter.
Figure 5A:
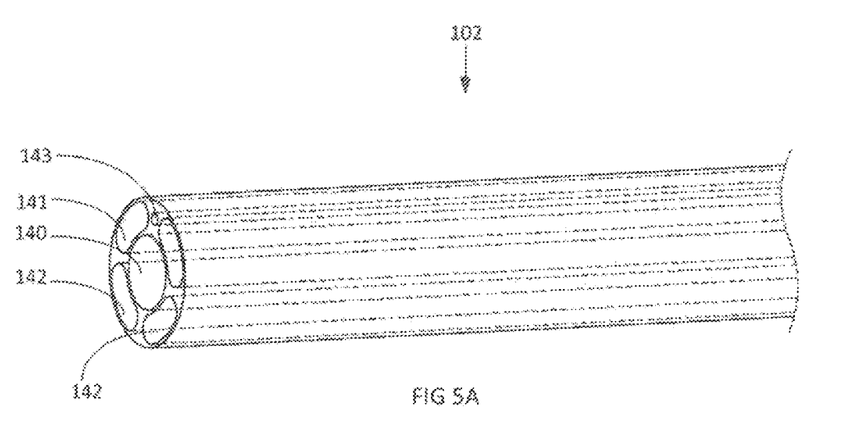
FIGS. 5A and 5B are perspective views of a lumen arrangement for a catheter body.
Figure 5B:
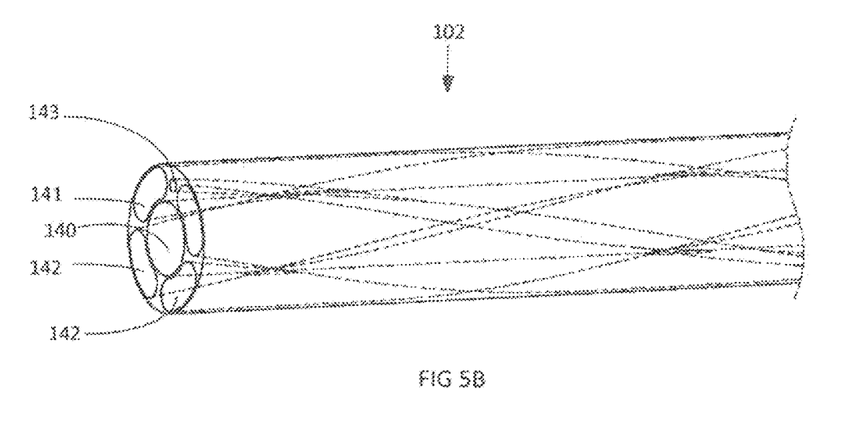

Within the catheter 100 are lumens 140, 141, 142 and 143, as shown, for example, in FIG. 2B. The lumens 140, 141, 142, 143 include a central or inner lumen 140, through which body fluid drained, surrounded, for example, by outer lumens 141, 142 associated with oil, and 143 for air for inflating the balloon 104. While plural (several) outer lumens 141, 142, 143 are shown any number of outer lumens is sufficient, provided there is a system for maintaining oil in, the catheter 100 walls (inner and outer), so as to allow for oil coating of the corresponding inner and/or outer surfaces of the catheter 100. There are lumens 143 associated with inflating, and deflating the balloon 104, While the inner 140 and outer lumens 141, 142, 143 are shown as straight, extending at least substantially parallel to each other along the length of the catheter 100, any one or more of the lumens 140-143 may be curved, circular, undulating, or other irregular shape, for example, as shown in FIGS. 5A and 5B.

FIGS. 6A-6J show various alternative lumen arrangements in the body 102. All of these alternative arrangements include at least one central lumen 140, for the drainage of body fluids, at least one oil filling lumen 141 connected, to the other lumen's to be filled with oil, at least one oil lumen 142, and at least one lumen 143 for air or other substances for inflating the balloon 104. For catheters lacking a balloon structure, all lumens are oil lumens 141, 142.

Figure 6A:
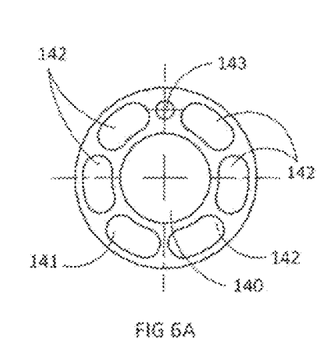
FIGS. 6A-6J are cross sectional views of alternative lumen arrangements for the catheter body of FIG. 1.
Figure 6B:
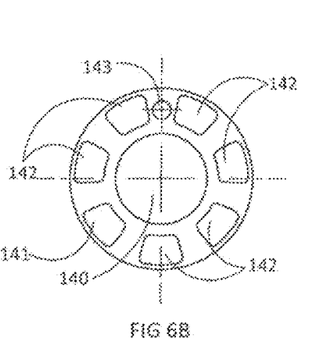
Figure 6C:
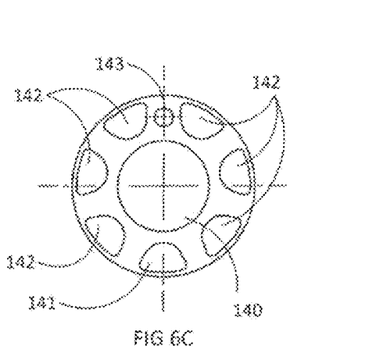
Figure 6D:
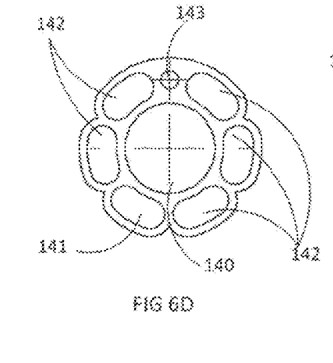
Figure 6E:
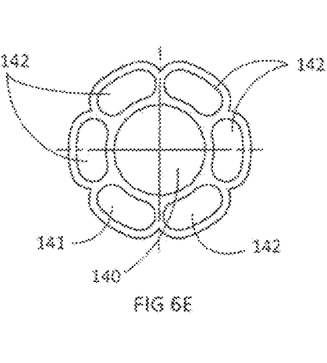
Figure 6F:
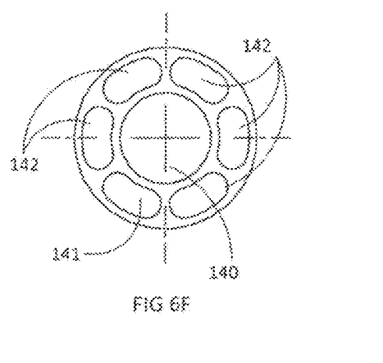
Figure 6G:
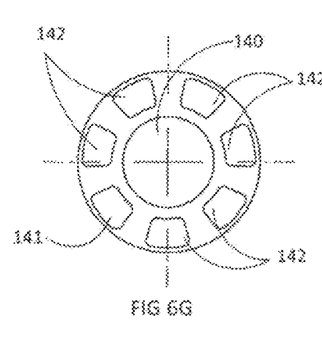
Figure 6H:
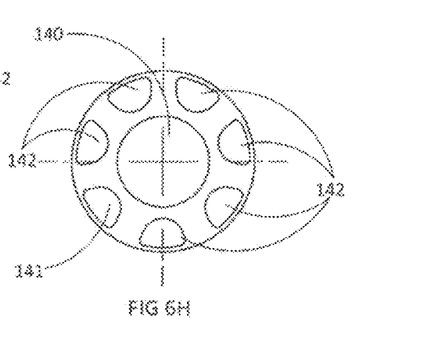
Figure 6I:
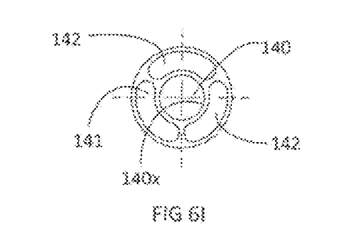
Figure 6J:
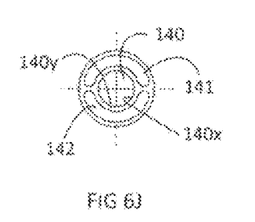

FIGS. 6D and 6E show an outer surface with longitudinal indentations for increasing the surface of the body to be covered with the leaching oil. Similar indentations can be along the inner surface of the body for the same purpose.

Figure 7A:
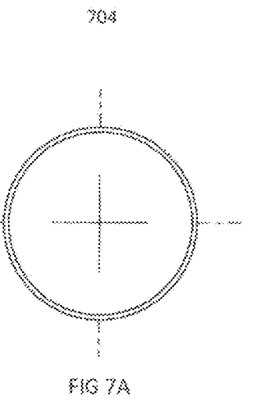
FIGS. 7A-7C and 8A-8C are cross-sectional views of alternative bodies for the catheter of FIG. 1.
Figure 7B:
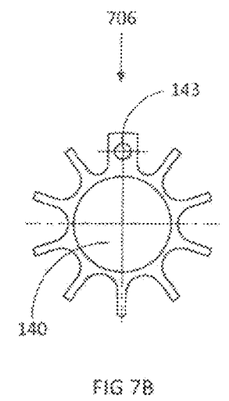
Figure 7C:
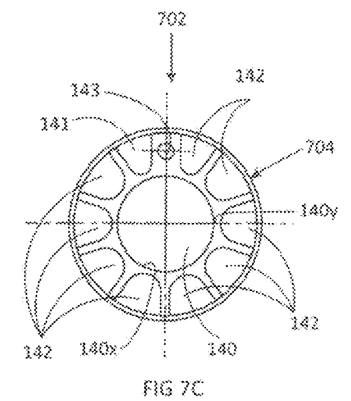

FIGS. 7A-7C shown an alternative embodiment, body 702 for the catheter 100. The outer tube 704 receives an inner core 706. The inner core 706 includes a central lumen 140, and a balloon inflation lumen 143, and as inserted into the outer tube 704 defines the oil filling 141 and oil lumens 142.

Figure 8A:
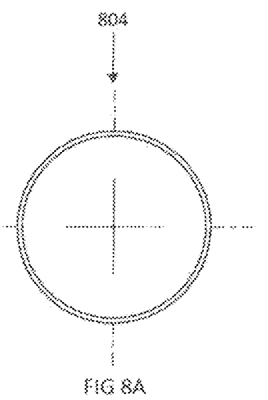
Figure 8B:
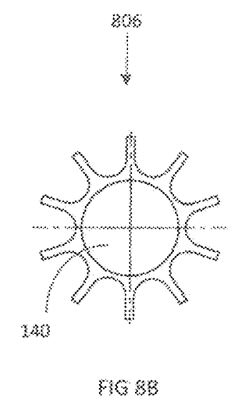
Figure 8C:
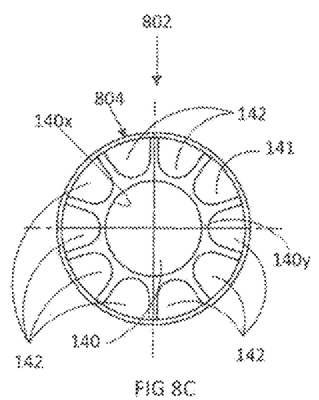

FIGS. 8A-8C shown an alternative embodiment body 802 for the catheter 100. The outer tube 804 receives and inner core 806. The inner core 806 includes a central lumen 140. As inserted into the outer tube 804, the core 806 defines the oil filling 141, oil lumens 142, and at least one balloon inflation lumen 143.

The inner cores 706, 806 and the outer tubes 704, 804 of the embodiments of FIGS. 7C and 8A-8C, may be from the same material or different materials to control the oil leaching and device flexibility.

Figure 9A:
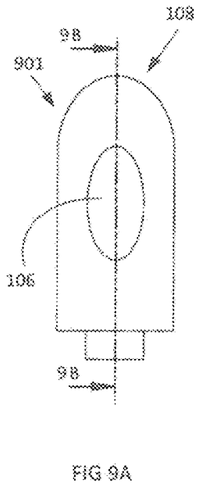
FIG. 9A is a front view of a tip of the catheter of FIG. 1.
Figure 9B:
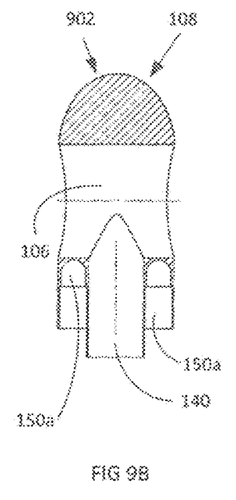
FIG. 9B is a longitudinal cross-sectional view of the tip of FIG. 9A taken along line 9B-9B.

FIGS. 9A and 9B show the tip 108 of the catheter 100. The tip 108 includes an outer portion 901 and an inner portion 902. The inner portion 902 includes a manifold 150a which connects all oil lumens 141, 142, such that oil from the oil filling lumen(s) 141 reaches the manifold 150a and flows into all of the one or more oil lumens 142, of the catheter body 102. The tip 108 includes the opening 106, single or multiple, through which urine and/or body fluids enter into the central lumen 140 of the body 102 for drainage, and has a spherical-like or rounded head 906.

Figure 10A:
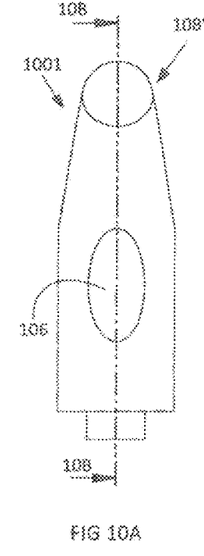
FIG. 10A, is a front view of an alternative embodiment of the tip of the catheter of FIG. 1.
Figure 10B:
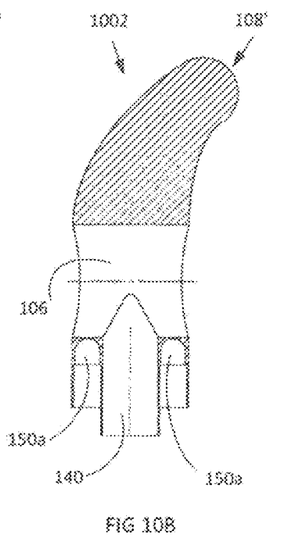
FIG. 10B is a longitudinal cross-sectional view of the tip of FIG. 10A taken along line 10B-10B.

FIGS. 10A and 10B show an alternative tip 108' for the catheter 100. This alternative tip 108' is similar to the tip 108, as detailed above, with similar structures in the corresponding "1000", except that the tip 108' includes a curved head 1006.

The bodies 102, 702, 802, and, outer tubes 704, 804, are made of, for example, Silastic® Elastomer (for example, Silastic® MDX4-4210 BioMedical Grade Elastomer), available from Dow Corning, which has a natural porosity. The outer walls 102x/outer tubes 704, 804 are of a thickness and porosity, which is, for example, the natural porosity and/or a modified porosity, of the material, to allow for leaching of oil from the lumens 141, 142 to the outer surfaces 102' of the body 102, and the outer surfaces 704', 804' of the respective outer tubes 704, 804. For example, the thickness of the outer wall 102x of the body 102 and the outer tubes 704, 804, is, for example, approximately 50 microns (micrometers) to approximately 600 microns, and, for example, approximately 100 microns to approximately 550 microns, for all materials. Such biocompatible silicones have a natural micro-porosity depending on the evaporated solvent used for forming the material. The aforementioned porosity/microporosity can also be a modified porosity.

Similarly, all other walls 140y of the oil filling 141 and oil 142 lumens bordering the central lumen 140 are in accordance (for example, material, thickness, porosity) with the aforementioned outer wall 102x of the body 102 and outer tubes 704. 804, so that oil leaches or penetrates the walls and coats the inner surface 140x of the central lumen 140.

The inner cores 706, 806 are also made, for example, of the aforementioned Silastic® Elastomer, available from Dow Corning. The outer tubes 704, 804 are joined to their respective inner cores 706, 806 by conventional polymeric joining techniques. Additional materials for the catheter body 102, outer tubes 704, 804 and cores 706, 806 include, for example, Polyvinyl Chloride, polyurethane, and other surgical grade polymeric materials.

Additional mico-pores may be drilled on the outer wall 102x and the outer tube 704, 804, as well as in the inner lumen wall for example, in portions which are the oil lumens 141, 142. These additional pores promote oil leaching through the outer wall 102x and outer tubes 706, 806 as well as the inner lumen. These pores range from approximately 2 microns to approximately 50 microns and allow control of the amount of oil to leach.

The oil used to fill the oil lumens 141, 142 is, for example, Superla Light Mineral Oil, Other medical grade mineral oils or vegetable oils, as well as oil-based substances are also suitable.

The catheter 100 may be prefilled with oil. In this case, the connector 110 does not have to be present. The oil lumen 141 is plugged (locked) to avoid leakage through the oil lumen 141 and out of the proximal end 100p of the catheter 100.

Figures 11A, 11B, 11C:
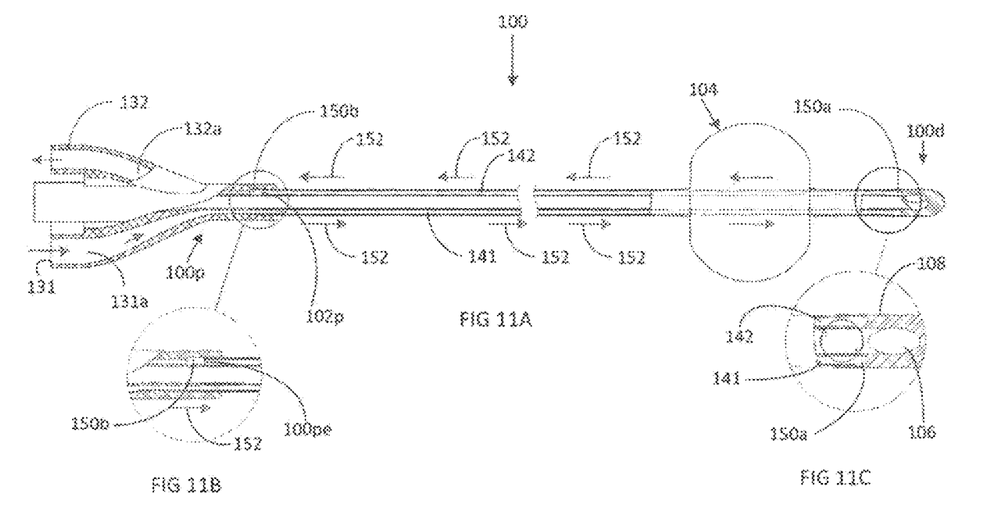
FIG. 11A is a cross-sectional longitudinal view of the catheter of FIG. 1 and the oil filling lumen of the catheter.
FIG. 11B is a cross sectional view detailing the vent at the connector of the catheter of FIG. 11A.
FIG. 11C is a cross-sectional view showing the manifold at the tip of the catheter of FIG. 11A.

FIGS. 11A-11C show oil filling of the catheter 100, with the oil flow indicated by arrows 152. The oil is filled through the port 131, which travels through the lumen 131a to the oil lumen 141. The oil flows through the manifold 150a at the tip 108. At the manifold 150a, oil enters the one or more oil lumens 142, with the oil flowing through each lumen 142 until the oil reaches the upper manifold 150b, which allows for venting the air which was in all of the oil lumens 141, 142) and the port 132.

FIGS. 12A-12C show oil filling of the catheter 100 with the alternative connector 110' and the air vent 132', with the oil flow indicated by the arrows 152', The oil flow is similar to that of FIGS. 11A-11C with oil flow through the oil lumens 142, The oil is filled through the port 131, which travels through the lumen 131a to the oil lumen 141. The oil flows through the manifold 150a at the tip into the oil lumens 142 until it reaches the upper manifold 150b, which directs air for venting through the vent port 132".

Figure 13:
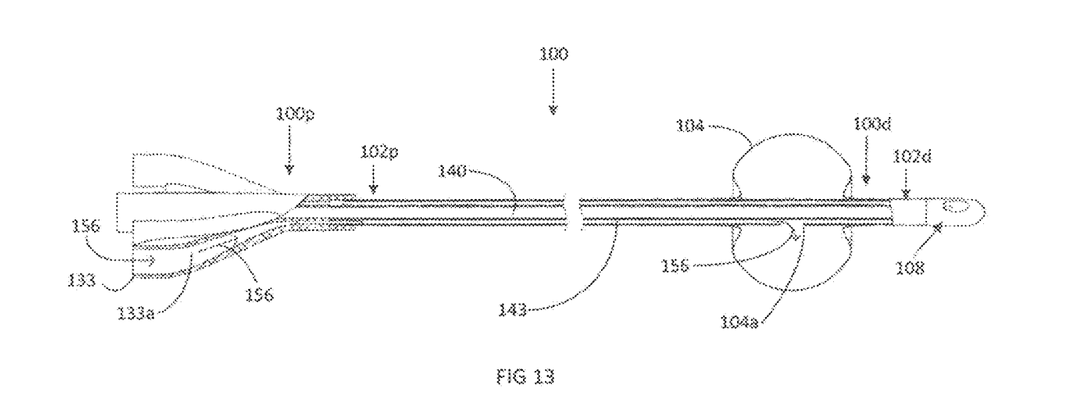
FIG. 13 is a partial cross sectional view of the catheter of FIG. 1 showing air flow for balloon inflation.

FIG. 13 shows the inflation of the balloon 104 of the catheter 100, with inflation air, oils or other oil-based substances, the flow indicated by the arrows 156. A syringe (not shown) introduces air to the port 133 of the connector, where the air (or other balloon 104 inflation substance) flows through the connector lumen 133a, and then through lumen 143 to the balloon 104. The air, oil, or oil-based substance, for inflation of the balloon 104, enters the balloon 104 through an opening 104a into the balloon 104 cavity.

While the catheter 100 is shown as a urinary catheter for urinary applications, such as urine drainage, the catheter 100 can be easily modified for use in other operations in other body locations and vessels, including other blood vessels, bile ducts and other ducts, and brain passageways and other tubular structures in the body. For example, tubes made in accordance with the invention may be double or other multiple layered tubes. Also, for example, devices may be such that they include polymeric walls, similar to that of the outer walls 102x of the catheter body 102, with inner or external membranes in which oil, as detailed above, is filled.

The present invention, while shown for human use, is also suitable for animal use.

FIGS. 14A, 14B, 14C, 14D and 15, show various structures for non-medical uses. These structures use materials, which are non-toxic and food quality materials. These structures are, for example, tubes, pipes and other conduits, both with multiple cross-sectional shapes, for use in fluid and liquid transport, delivery, storage, and the like.

Figure 14A:
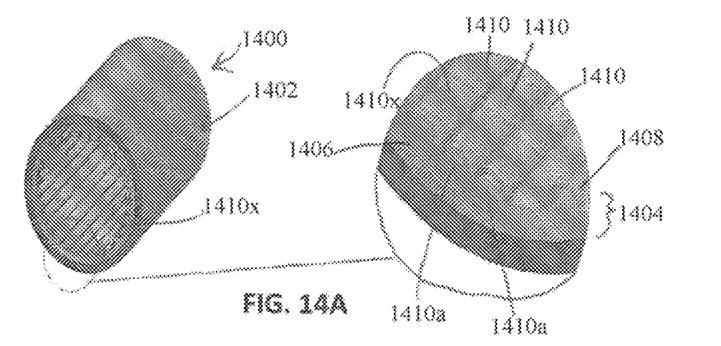
FIGS. 14A and 14B are cross-sectional perspective views of pipes in accordance with other embodiments of the present invention.
Figure 14B:
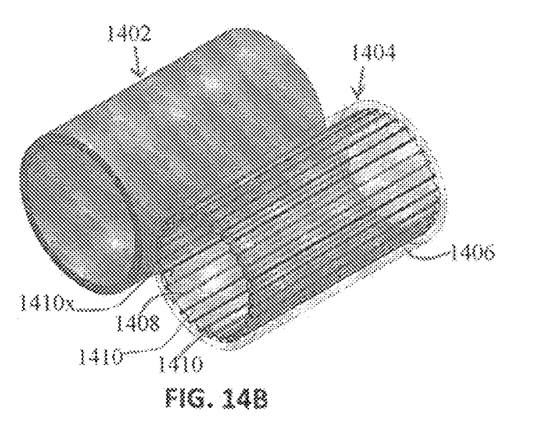
Figure 14C:
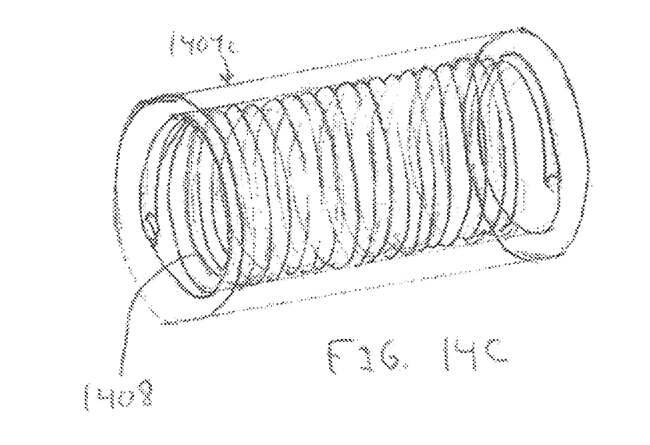
FIGS. 14C and 14D are alternate inner tubes to the inner tube of FIGS. 14A and 14B.
Figure 14D:
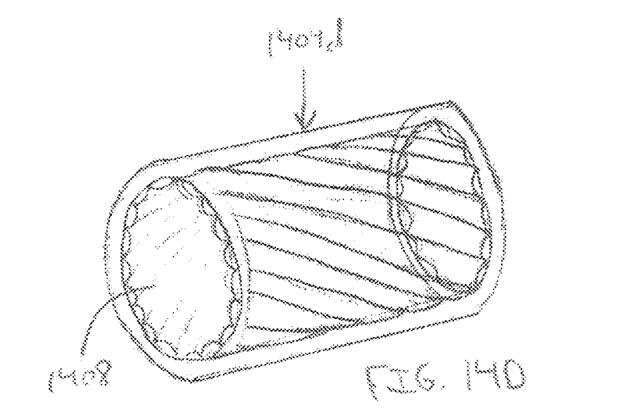

FIGS. 14A and 14B show tubes 1400 in accordance with embodiments of the present invention, which may be used as pipes, conduits and the like for carrying water and other water-based liquids. The tubes 1400 are typically of an outer tube 1402, which, defines an outer layer, and an inner tube 1404, which when in the outer tube 1002, defines an intermediate layer or tube 1406, and an inner layer or tube 1408. The inner layer 1408 includes channels 1410, which are expandable, from an initially flat orientation to a rounded shape, when the internal lumens 1410a are filled with oil. The inner layer 1408, for example, the channels 1410 of this inner layer 1408 are arranged, in orientations such as longitudinal, spiraling (coiled), such as a single "hard" coil 1408 of tube 1404c (FIG. 14C), or a multiple spiraling channels 1408 of tube 1404d (FIG. 14D) or zig-zaging. The inner layer 1408 is of a material, with a thickness and porosity, which allows the oil to leach or penetrate the inner layer 1408 and coat the inner surface 1410x of the tube 1400, similar to that detailed for tubes 704, 804, above.

The outer tube 1402 and intermediate tube 1406 are, for example, of a metal or polymeric material. The inner tube 1408, with the channels 1410, is, for example, made of the aforementioned Silastic® Elastomer, available from Dow Corning. The oil used, is, for example, Superla Light Mineral Oil, Other medical grade mineral oils or vegetable oils, as well as oil-based substances are also suitable. The tubes 1400 are either filled with oil on deployment or pre-filled with oil, or combinations thereof.

Figure 15:
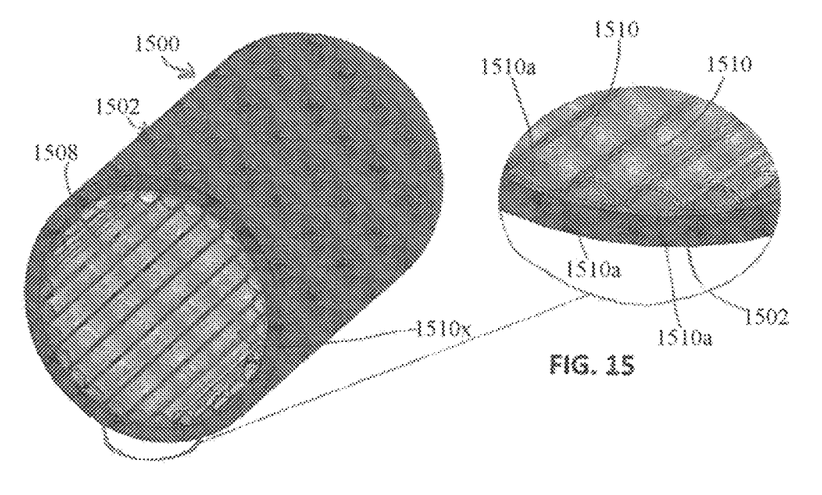
FIG. 15 is a cross-sectional perspective views of a pipe in accordance with other embodiments of the present invention; and, FIG. 16 is a diagram of a water delivery system.

FIG. 15 shows a pipe 1500 formed of an outer tube 1502 and an inner surface 1508, formed of channels 1510, for example, longitudinal, spiraling (coiled) or zig-zaging channels, defining lumens 1510a, similar to the inner layer 1408 and channels 1410 of the tubes 1400 detailed in FIGS. 14A and 14B above. The channels 1510, in the lumens 1510a, are designed to be filled with oil, and are of a material, with a thickness and porosity, which, allows the oil to leach or penetrate the inner layer 1408, and coats the inner surface 1510x of the tube 1500, similar to that detailed for tubes 704, 804, above. The inner layer 1508 is, for example, in a flat orientation, with the channels 1510 becoming rounded, when the lumens 1510a are filled with oil.

The outer tube 1502 is, for example, of a polymeric material. The inner tube 1508, with the channels 1510, is, for example, made of the aforementioned Silastic® Elastomer, available from Dow Corning. The outer tube 1502 may also be a polymeric pipe, coextruded with the material of the inner layer 1508.

The oil used, is, for example, Superla Light Mineral Oil. Other medical grade mineral oils or vegetable oils, as well as oil-based substances are also suitable. The tubes 1500 are either filled with oil on deployment or pre-filled with oil, or combinations thereof.

The structures of FIGS. 14A, 14B and 15, while shown as tubes and pipes are also usable in non-medical applications, such as, water transport pipes in municipal water systems, pipes and conduits in water transport tankers and trucks, pipes and conduits in liquid food (i.e., milk) transport tankers, and in brine and waste-water tankers. These structures are also usable as, industrial water transport pipes, and sewer transport pipes.

The descriptions of the various embodiments of the present invention have been presented for purposes of illustration, but are not intended to be exhaustive or limited to the embodiments s disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A tube comprising:
    a body including a lumen bounded at least in part by an outer wall of the body, the outer wall being made of a material selected to allow oil to leach through the outer wall of the body and onto an outer surface of the outer wall of the body in a process involving an interaction between the outer wall material and the oil, to form a coating on the outer surface of the outer wall of the body;
    said lumen comprising a vent joined to a manifold and configured to allow air to escape from the lumen as the lumen is being filled with oil, wherein an increase in oil pressure is prevented and oil is prevented from escaping through said vent.

2. The tube of claim 1, wherein the lumen extends along the outer wall of the body.

3. The tube of claim 2, wherein the lumen extends along the outer wall of the body in at least one of a longitudinal orientation, a spiral orientation, and a zig-zag orientation.

4. The tube of claim 3, wherein the lumen is filled with the oil.

5. The tube of claim 1, wherein the lumen includes: a central lumen extending through the body, and at least one internal lumen intermediate the central lumen and the outer wall of the body, a portion of the central lumen bordering the at least one internal lumen defining an inner wall made of a material selected to allow the oil to leach through the inner wall and onto an inner surface of the central lumen in a process involving an interaction between the inner wall material and the oil, to form a coating on the inner surface of the central lumen.

6. The tube of claim 5, wherein the at least one internal lumen is filled with the oil.

7. The tube of claim 6, wherein the oil includes oil-based substances.

8. The tube of claim 5, wherein the material of the inner wall and a material of the outer wall are of a porosity to accommodate the oil leaching from the at least one internal lumen through the inner wall to a surface of the inner wall and through the outer wall to the outer surface of the outer wall.

9. A device comprising:
    an external surface covered with a silicone membrane under which oil is filled, the silicone membrane configured to allow the oil to leach therethrough to a surface of the silicon membrane in a process involving an interaction between a material of the silicone membrane and the oil, and form a coating on an outer surface of the body;
    said lumen comprising a vent joined to a manifold and configured to allow air to escape from the lumen as the lumen is being filled with oil, wherein an increase in oil pressure is prevented and oil is prevented from escaping through said vent.

10. The device of claim 9, which is at least one of an implantable device and an indwelling device.

11. The device of claim 10, wherein the oil includes oil-based substances.

12. The device of claim 11, wherein the silicone membrane is of a porosity to accommodate the oil leaching therethrough to the surface of the silicone membrane.

13. A device comprising: a double layer membrane surrounding a lumen configured for leaching oil therethrough, in which the oil is filled between layers of the double membrane structure and leaches to an outer surface of the double membrane and form a coating on the outer surface of the body:
    a) said lumen comprising a vent joined to a manifold and configured to allow air to escape from the lumen as the lumen is being filled with oil, wherein an increase in oil pressure is prevented and oil is prevented from escaping through said vent.

14. The device of claim 13, wherein the double layer membrane includes silicone.

15. The device of claim 14, which is at least one of an implantable device and an indwelling device.

16. The device of claim 13, wherein the oil includes oil-based substances.

17. The device of claim 15, wherein the double layer membrane is of a porosity to accommodate the oil leaching therethrough to the surface of the device.

18. A conduit comprising:
    an outer tubular member; and,
    an inner surface including a plurality of channels extending along the tubular member, the inner surface of a material configured for leaching oil therethrough in a process involving an interaction between the inner surface material and the oil, when the channels are filled with the oil to form a coating on an outer surface of the body;
    said lumen comprising a vent joined to a manifold and configured to allow air to escape from the lumen as the lumen is being filled with oil, wherein an increase in oil pressure is prevented and oil is prevented from escaping through said vent.

19. The conduit of claim 18, wherein the channels are oriented substantially parallel to each other and extend along a length of the outer tubular member.

20. The conduit of claim 18, wherein the channels are oriented in a spiraling manner along a length of the outer tubular member.

21. The conduit of claim 20, wherein the channels oriented in the spiraling manner include a single channel oriented in the spiraling manner.

22. The conduit of claim 20, wherein the channels oriented in the spiraling manner include multiple channels oriented in the spiraling manner.

23. The conduit of claim 20, wherein the outer tubular member includes an outer layer in communication with an inner layer defining the inner surface.

24. The conduit of claim 23, wherein the outer tubular member and the inner surface are coextruded.

25. The conduit of claim 20, including at least one of tubes and pipes.

26. The conduit of claim 20, wherein the material is of a porosity for accommodating the oil to leach therethrough and coat the inner surface.

27. A method for inhibiting biofilm formation in a structure comprising:
    providing the structure including at least one lumen for holding oil, the structure including at least one member defining a side of the at least one lumen, the at least one member of a material configured for leaching the oil through the at least one member to an outer surface of the at least one member in a process involving an interaction between the material of the at least one member and the oil, to form a coating on an outer surface of the body, when the at least one lumen is filled with the oil; and, filling the at least one lumen with oil;
    said lumen comprising a vent joined to a manifold and configured to allow air to escape from the lumen as the lumen is being filled with oil, wherein an increase in oil pressure is prevented and oil is prevented from escaping through said vent.

28. The method of claim 27, wherein the structure includes at least one of: implantable medical devices, indwelling catheters, medical tubes, medical conduits, non-medical tubes, non-medical conduits and pipes.

29. The method of claim 28, additionally comprising: deploying the structure to a designated site.

30. The method of claim 27, wherein the oil includes oil-based substances.

31. The method of claim 30, wherein the oil-based substances include at least one of: medical grade mineral oils, mineral oils, and vegetable oils.

32. The method of claim 27, wherein the material is of a porosity for accommodating the oil to leach therethrough to an outer surface of the material.

\* \* \* \* \*